United States Patent [19]

Cheng

[11] Patent Number: 4,679,036
[45] Date of Patent: Jul. 7, 1987

[54] SIGNALLING DEVICE FOR INDICATING A NURSED PERSON IN A BAD SLEEPING CONDITION

[76] Inventor: Tseng-Yng Cheng, 31, Lane 98, Chien Hsing Road, Chung Li City, Taiwan

[21] Appl. No.: 728,178

[22] Filed: Apr. 29, 1985

[51] Int. Cl.[4] .............................................. G08B 23/00
[52] U.S. Cl. .................................... 340/573; 340/521; 340/540; 128/782
[58] Field of Search ............... 340/573, 540, 568, 521; 128/782; 5/494

[56] References Cited

U.S. PATENT DOCUMENTS

| | | | |
|---|---|---|---|
| 4,348,562 | 9/1982 | Florin | 340/573 |
| 4,411,034 | 10/1983 | Williams | 340/568 |
| 4,539,559 | 9/1985 | Kelly et al. | 340/573 |
| 4,614,939 | 9/1986 | Wang | 340/573 |

FOREIGN PATENT DOCUMENTS 958098 11/1974 Canada ................................ 340/573

OTHER PUBLICATIONS

"Babycom"; *Practical Electronics;* Nov. 1979, pp. 24–27.
"A Temp. Monitoring System for Use on Normal Newborn Infants" *IEEE Trans. Instrum. & Meas.* vol. IM-21, No. 1, Feb. 1972, Parrish.

*Primary Examiner*—James L. Rowland
*Assistant Examiner*—Jeffery A. Hofsass
*Attorney, Agent, or Firm*—Ladas & Parry

[57] ABSTRACT

The present invention discloses a signalling device for indicating a person, who is being nursed, in a bad sleeping condition comprising:

means for detecting the bad sleeping condition, adapted to be mounted on the body of the person for outputting a voltage signal when the bad sleeping condition is detected;

a switching circuit coupled to the detecting means;

a signal generating circuit coupled to the switching circuit for being turned on by the switching circuit in response to the voltage signal from the detecting means in order to output an alarm signal; and a frequency modulating circuit coupled to the switching circuit for being turned on thereby in response to the voltage signal, and also coupled to the signal generating circuit for receiving the alarm signal and frequency modulating it to radiate out a radio wave which is adapted to be received and reproduced by an FM receiver in order to signal that the nursed person is in the bad sleeping condition.

3 Claims, 9 Drawing Figures 4,679,036

SIGNALLING DEVICE FOR INDICATING A NURSED PERSON IN A BAD SLEEPING CONDITION

BACKGROUND OF THE INVENTION

The present invention is related to a signalling device of bad sleeping condition, and more particularly to a signalling device for indicating a person, who is being nursed, such as an infant, an old person, or a patient, in such bad sleeping conditions as the quilt moved away, and the nursed person wetting to the bed.

One type of the generally used signalling devices of bad sleeping condition for an infant utilizes a photoelectric sensing element to act as a trigger element, and an alarm element connected to the photoelectric sensing element through a relatively long line thus the alarm element may arrange far away from the infant. The signalling device is tied on the body of the infant by an elongated belt and is allocated under the quilt which covers on the infant when it is used. During the night, above the infant, a night light must be turned on for making the photoelectric sensing element still capable of sensing light so as to trigger the alarm element, in the event that the quilt is moved away from the infant's body. Although the conventional signalling device can provide the parents or nurse with many conveniences, it still has the following drawbacks:

(a). The elongated belt tied around the stomach of the infant will cause uncomfortableness.

(b). The ambient illumination varies to such a large extent from day to night and from sunny to cloudy day that the photoelectric sensing element might often operate wrongly.

(c). The separate arrangement of the photoelectric sensing element and the alarm element causes a more complicated manufacturing process, resulting in a high production cost.

(d). The line connected between the photoelectric sensing element and the alarm element might be inadequately wound on the infant's body, resulting in the damage to the infant.

(e). Since the length of the line is fixed, the arrangement of the photoelectric sensing element and the alarm element is limited within an extent.

A signalling device in accordance with one preferred embodiment of the present invention intends to improve on the drawbacks described above.

SUMMARY OF THE INVENTION

One object of the present invention is to provide a signalling device of bad sleeping condition which utilizes a frequency modulating circuit to radiate out a radio wave of alarm signal when the bad sleeping condition is detected, and that the line connected between the sensing section and the alarm section is no longer needed.

Another object of the present invention is to provide a signalling device which simplifies the manufacturing process, and decreases the production cost.

In accordance with the present invention, a signalling device for indicating a person, who is being nursed, in a bad sleeping condition comprises:

means for detecting said bad sleeping condition, adapted to be mounted on the body of said person for outputting a voltage signal when said bad sleeping condition is detected;

a switching circuit coupled to said detecting means;

a signal generating circuit coupled to said switching circuit for being turned on by said switching circuit in response to said voltage signal from said detecting means in order to output an alarm signal; and a frequency modulating circuit coupled to said switching circuit for being turned on thereby in response to said voltage signal, and also coupled to said signal generating circuit for receiving said alarm signal and frequency modulating it to radiate out a radio wave which is adapted to be received and reproduced by an FM receiver in order to signal that said nursed person is in said bad sleeping condition.

BRIEF DESCRIPTION OF THE DRAWINGS

The present invention will be more fully understood from the following detailed description, taken in connection with the accompanying drawings which form an integral part of this application and in which.

DETAILED DESCRIPTION OF THE PREFERRED EMBODIMENTS

Figure 1:
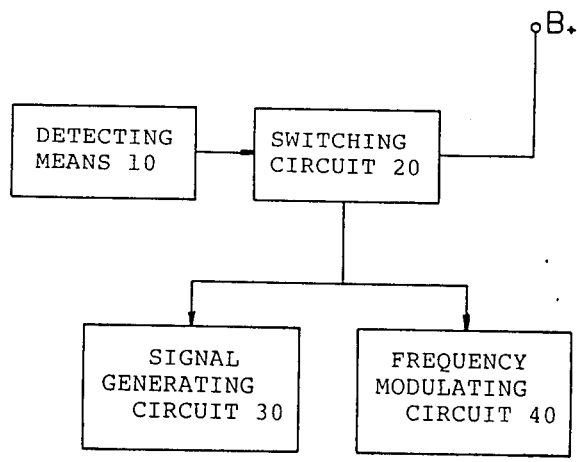
FIG. 1 is a block diagram of the signalling device in accordance with the present invention.

Referring now to the drawings, it should be noted that a like member is designated with a like reference number. In FIG. 1, there is shown a block diagram of the signalling device which includes means for detecting the bad condition 10, a switching circuit 20, a signal generating circuit 30, and a frequency modulating circuit 40. The detecting means 10 will output a voltage signal when the bad condition is detected, and the switching circuit 20 coupled to the detecting means 10 is constructed to receive the voltage signal to turn on the signal generating circuit 30 and the frequency modulating circuit 40, which are all coupled to the switching circuit 20. The signal generating circuit 30 will output an alarm signal when it is turned on, and the frequency modulating circuit 40 coupled to the signal generating circuit 40 is constructed to receive and frequency modulate the alarm signal to radiate out a radio wave. This radio wave is adapted to be received and reproduced by an FM receiver, which is allocated within an appropriate extent, in order to signal the parents or nurse that the nursed person is in the bad sleeping condition.

Figure 2:
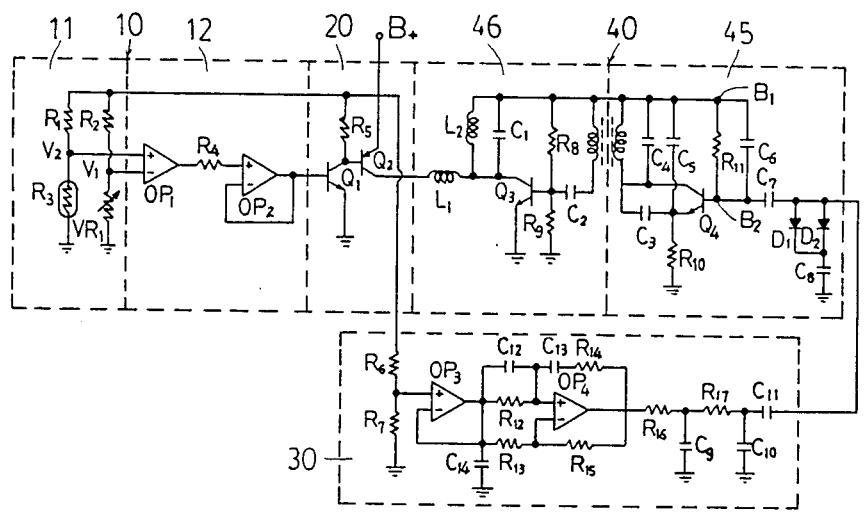
FIG. 2 is a schematic electrical diagram of the signalling device according to one preferred embodiment.
Figure 8:
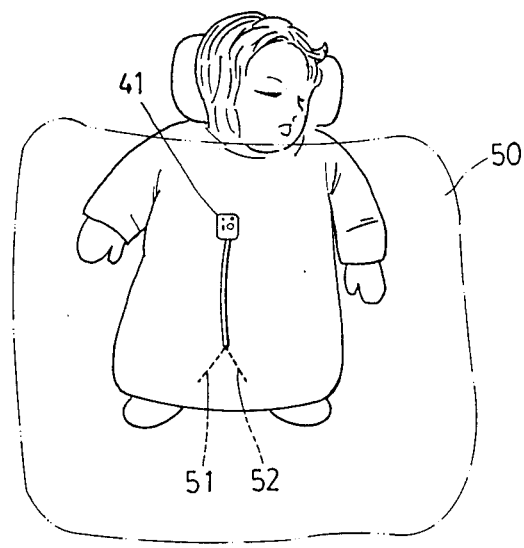
FIG. 8 is a schematic view illustrating the signalling device to be mounted on the body of an infant.

In one embodiment of the present invention, the bad sleeping conditon may be the quilt 50 covered on the nursed person, as shown in FIG. 8, to be moved away from the nursed person's body. In this case, the electrical circuit of the signalling device of the present invention is shown in FIG. 2 in detail. The detecting means 10 includes a detecting circuit 11 which has a thermistor R3 capable of varying its resistance value in accordance with the temperature value upon the nursed person's body, provided therein, and a comparator 12 coupled to the thermistor R3 at its positive input terminal, connected to a reference voltage at its negative input terminal, and coupled to the switching circuit 20 at its output section. In this case, the thermistor R3 has a negative temperature coefficient, i.e. when the ambient temperature increases, its resistance decreases, whereas when the temperature decreases, its resistance increases. It should be noted that if the thermistor has a positive temperature coefficient, the connection of the detecting circuit 11 can be easily modified by those who are ordinarily skilled in the art. When the quilt 50 is moved away from the nursed person's body by his kick or other conditions, the temperature around the termistor R3 will decrease, as a result, the voltage appeared at the point V2 gradually rises until it is greater than the voltage appeared at the point V1. Then, the comparator 12, which includes a differential amplifier OP1 and a operation amplifier OP2, will actuate the switching circuit 20 to turn on, so that the DC electrical power B+ is supplied to the signal generating circuit 30 and the frequency modulating circuit 40. The frequency modulating circuit 40 includes a frequency modulating section 45 coupled to the signal generating circuit 30 for receiving and frequency modulating the alarm signal, and an radiating section 46 coupled to the frequency modulating section 45 for radiating out the modulated alarm signal.

When the quilt 50 normally covers on the nursed person's body, the resistance of the termistor R3 is so low that the voltage at V2 is smaller than the voltage at V1. As a result, the switching circuit 20 is turned off, and the electrical power is interrupted to supply to the signal generating circuit 30 and the frequency modulating circuit 40.

Figure 3:
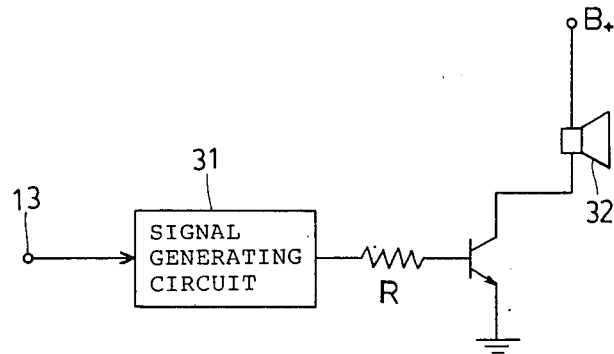
FIG. 3 is a schematic electrical diagram of an alarm circuit.
Figure 4:
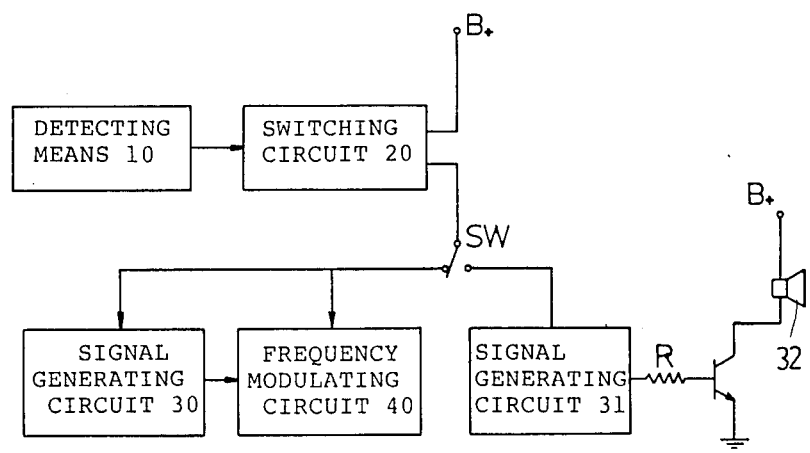
FIG. 4 is a block diagram of the signalling device incorporated with the alarm circuit of FIG. 3.

It should be noted that in this embodiment the signal generating circuit 30 may be a low-frequency oscillation circuit, or a phonic integral circuit or music integral circuit. It should also be noted that an alarm element shown in FIG. 3 similar to the art can be further connected to the switching circuit 20 through a switch SW for being selected to directly signal from its speaker 32, as shown in FIG. 4.

Figures 5A, 5B:
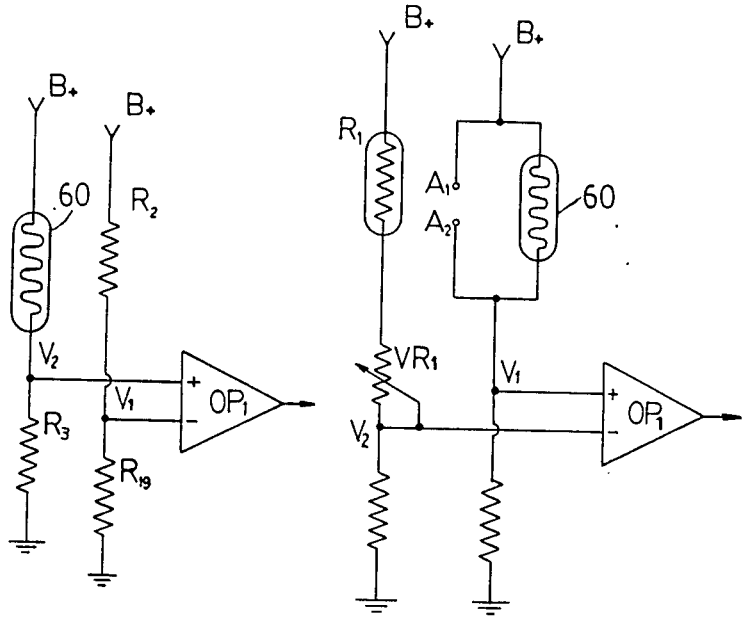
FIGS. 5(a) and 5(b) are schematic electrical diagrams of two preferred embodiment of detecting means in accordance with the present invention.

Referring to FIG. 5(a), a photo varistor 60 can be utilized to substitute for the thermistor in order to vary its resistance value in response to the illumination upon the person's body, and to actuate the switching circuit 20 as the manner described above. Also, both of the photo varistor 60 and the thermistor can be all used as shown in FIG. 5(b). In this embodiment, the photo varistor 60 is preferably a cadmium sulphide photo varistor.

The bad condition may also be that the nursed person has urinated on the bed. In this case, the detecting circuit 10 further includes a pair of separate contacts 51 and 52 with their one terminals respectively connected to A1 and A2 shown in FIG. 5(b) and the other terminals separately mounted on a diaper used by the nursed person as shown in FIG. 8. When the diaper is wetted, the contacts 51 and 52 are connected due to the conductivity of liquid, as a result, the comparator 12 actuates the switching circuit 20 as the manner described above.

Figure 6:
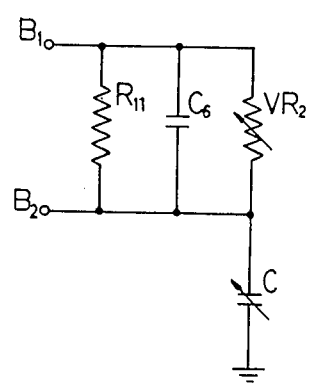
FIG. 6 is a schematic electrical diagram of a microphone circuit which could be connected in the frequency modulating circuit of the present invention.

Referring to FIG. 6, a microphone circuit including a microphone C can be used to substitute the right portion from the line B1–B2 in the frequency modulating circuit 40 (including R11) shown in FIG. 2. Then, the microphone circuit can be actuated by the sound waves that the nursed person makes, and the frequency modulating section 45 and the radiating section 46 will modulate the equivalent signal of the sound waves to radiate out a radio wave. Therefore, any sounds the nursed person makes can also be monitored.

Figure 7:
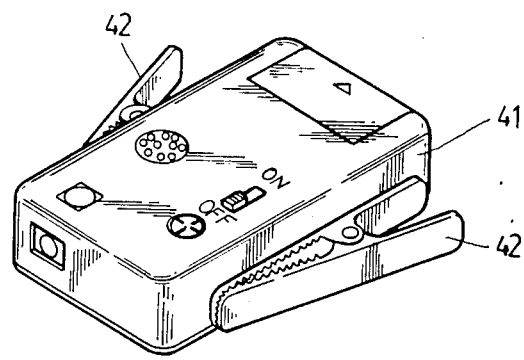
FIG. 7 is a perspective view of the signalling device illustrating that all the electrical circuits are arranged inside a casing.

Referring to FIG. 7, all of the electrical circuits of the signalling device can be arranged within a casing 41. two clips 42 are respectively secured on two sides of the casing 41 for fixing the signalling device onto the cloth worn by the nursed person and just under the quilt 50. In this way, the nursed person will no longer feel uncomfortable when the signalling device of the present invention is mounted on the body of the nursed person.

While the invention has been described in connection with what is presently considered to be the most practical and preferred embodiment, it is to be understood that the invention is not to be limited to the disclosed embodiment but on the contrary, is intended to cover various modifications and equivalent arrangements included within the spirit and scope of the appended claims which scope is to be accorded the broadest interpretation so as to encompass all such modification and equivalent structures.

What is claimed is:

1. A signalling device for indicating a person, who is being nursed, in a bad sleeping condition comprising: means for detecting said bad sleeping condition, adapted to be mounted on the body of said person for outputting a voltage signal when said bad sleeping condition is detected; a switching circuit coupled to said detecting means; a signal generating circuit coupled to said switching circuit for being turned on by said switching circuit is response to said voltage signal from said detecting means in order to output an alarm signal; and a frequency modulating circuit coupled to said switching circuit for being turned on thereby in response to said voltage signal, and also coupled to said signal generating circuit for receiving said alarm signal and frequency modulating it to radiate out a radio wave which is adapted to be received and reproduced by an FM receiver in order to signal that said nursed person is in said bad sleeping condition; the detecting means consisting of a detecting circuit containing a combination of sensors, one of said sensors being sensitive to light, one of said sensors being sensitive to temperature, and one of said sensors being sensitive to urination, any which of said sensors being capable of detecting a bad sleeping condition, wherein the temperature sensor is a thermistor capable of varying its resistance value in accordance with the temperature value on said person's body is provided, and a comparator is coupled to said thermistor at one input terminal thereof, connected to a reference voltage at the other input terminal, and coupled to said switching circuit at the output section thereof, so that when said quilt is moved away from the person's body, the temperature value around said thermistor decreases, causing said comparator to actuate said switching circuit to turn on said signal generating circuit and said frequency modulating circuit in response to the variation of resistance value of said thermistor.

2. A signalling device as claimed in claim 1, wherein said thermistor has a negative temperature coefficient.

3. A signalling device as claimed in claim 2, wherein said comparator is a differential amplifier.

* * * * *